United States Patent
Ishikawa et al.

(10) Patent No.: US 10,047,351 B2
(45) Date of Patent: Aug. 14, 2018

(54) CELLOBIOHYDROLASE HAVING IMPROVED THERMAL STABILITY

(71) Applicant: NATIONAL INSTITUTE OF ADVANCED INDUSTRIAL SCIENCE AND TECHNOLOGY, Tokyo (JP)

(72) Inventors: Kazuhiko Ishikawa, Osaka (JP); Seiichiro Kishishita, Hiroshima (JP); Makoto Nakabayashi, Hiroshima (JP); Saori Kamachi, Hiroshima (JP); Toshiaki Yanamoto, Hiroshima (JP); Tatsuya Fujii, Hiroshima (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 15/313,784

(22) PCT Filed: May 26, 2015

(86) PCT No.: PCT/JP2015/064994
§ 371 (c)(1),
(2) Date: Nov. 23, 2016

(87) PCT Pub. No.: WO2015/182570
PCT Pub. Date: Dec. 3, 2015

(65) Prior Publication Data
US 2017/0191048 A1  Jul. 6, 2017

(30) Foreign Application Priority Data

May 27, 2014  (JP) ................................ 2014-109035

(51) Int. Cl.
*C12N 9/42* (2006.01)
*C12N 9/24* (2006.01)
*C12P 21/06* (2006.01)
*C12P 19/34* (2006.01)
*C12N 15/00* (2006.01)
*C12N 1/20* (2006.01)
*C12N 1/00* (2006.01)
*C07H 21/04* (2006.01)
*C07K 1/00* (2006.01)
*C12P 19/12* (2006.01)
*C12P 19/14* (2006.01)

(52) U.S. Cl.
CPC ............ *C12N 9/2437* (2013.01); *C12P 19/12* (2013.01); *C12P 19/14* (2013.01); *C12Y 302/01091* (2013.01)

(58) Field of Classification Search
CPC ........... C12N 9/2437; C12Y 302/01091; C12P 19/12; C12P 19/14

USPC ....... 435/209, 200, 69.1, 91.1, 320.1, 252.3, 435/254.11; 536/23.1, 23.2; 530/350
See application file for complete search history.

(56) References Cited

U.S. PATENT DOCUMENTS 8,101,393 B2 * 1/2012 Gray .................... C12N 9/2402
424/94.61
9,234,216 B2 * 1/2016 Stege ............... C12Y 302/0109
2015/0044728 A1   2/2015 Fukuura et al.

FOREIGN PATENT DOCUMENTS

| JP | 2001-017180 A | 1/2001 |
| JP | 2006-515506 A | 6/2006 |
| JP | 2012-039967 A | 3/2012 |
| WO | 2004/016760 A2 | 2/2004 |
| WO | 2012/104239 A1 | 8/2012 |
| WO | 2013/103127 A1 | 7/2013 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Voutilainen et al., "Expression of Talaromyces emersonii cellobiohydrolase Cel7A in *Saccharomyces cerevisiae* and rational mutagenesis to improve its theromostability and activity", Protein Engineering, Design & Selection, 23: 39-79 (2010).
Gusakov, "Alternatives to Trichoderma reesei in biofuel production", Trends in Biotechnology, 29: 419-425 (2011).
Fang et al., "Strain improvement of Acremonium cellulolyticus for cellulase production by mutation", Journal of Bioscience and Bioengineering, 107: 256-261 (2009).
Inoue et al., "Construction of a starch-inducible homologous expression system to produce cellulolytic enzymes from Acremonium cellulolyticus", J. Ind. Microbiol. Biotechnol., 40: 823-830 (2013).
Kishishita et al., "Cellulose-inducible xylanase Xyl10A from Acremonium cellulolyticus: Purification, cloning and homologous expression", Protein Expression and Purification, 94: 40-45 (2014).

(Continued)

*Primary Examiner* — Ganapathirama Raghu
(74) *Attorney, Agent, or Firm* — Morgan, Lewis & Bockius LLP

(57) ABSTRACT

The disclosure provides a polypeptide with a mutation having cellobiohydrolase activity and improved thermal stability.

20 Claims, 2 Drawing Sheets

(56) References Cited

OTHER PUBLICATIONS

Grassick et al., "Three-dimensional structure of a thermostable native cellobiohydrolase, CBH IB, and molecular characterization of the cel7 gene from the filamentous fungus, *Talaromyces emersonii*", European Journal of Biochemistry, 271: 4495-4506 (2004).

Office Action issued in corresponding Japanese Patent Application No. 2016-523493, dated Jun. 12, 2018.

\* cited by examiner

SEQUENCE LISTING

```
<160> NUMBER OF SEQ ID NOS: 18

<210> SEQ ID NO 1
<211> LENGTH: 529
<212> TYPE: PRT
<213> ORGANISM: Talaromyces cellulolyticus

<400> SEQUENCE: 1

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
                20                  25                  30

Ala Glu Thr His Pro Ser Leu Ser Trp Ser Thr Cys Lys Ser Gly Gly
            35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Ser Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Ile Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300
```

```
Thr Lys Pro Phe Thr Val Val Thr Gln Phe Val Thr Asn Asp Gly Thr
305                 310                 315                 320

Ser Thr Gly Ser Leu Ser Glu Ile Arg Arg Tyr Tyr Val Gln Asn Gly
            325                 330                 335

Val Val Ile Pro Gln Pro Ser Ser Lys Ile Ser Gly Ile Ser Gly Asn
            340                 345                 350

Val Ile Asn Ser Asp Tyr Cys Ala Ala Glu Ile Ser Thr Phe Gly Gly
            355                 360                 365

Thr Ala Ser Phe Ser Lys His Gly Gly Leu Thr Asn Met Ala Ala Gly
        370                 375                 380

Met Glu Ala Gly Met Val Leu Val Met Ser Leu Trp Asp Asp Tyr Ala
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Thr Cys Ala Thr Thr Ser Gly Asp Pro
                420                 425                 430

Lys Thr Val Glu Ala Gln Ser Gly Ser Ser Tyr Val Thr Phe Ser Asp
            435                 440                 445

Ile Arg Val Gly Pro Phe Asn Ser Thr Phe Ser Gly Gly Ser Ser Thr
450                 455                 460

Gly Gly Ser Thr Thr Thr Thr Ala Ser Arg Thr Thr Thr Thr Ser Ala
465                 470                 475                 480

Ser Ser Thr Ser Thr Ser Ser Thr Ser Thr Gly Thr Gly Val Ala Gly
                485                 490                 495

His Trp Gly Gln Cys Gly Gly Gln Gly Trp Thr Gly Pro Thr Thr Cys
            500                 505                 510

Val Ser Gly Thr Thr Cys Thr Val Val Asn Pro Tyr Tyr Ser Gln Cys
            515                 520                 525

Leu

<210> SEQ ID NO 2
<211> LENGTH: 5
<212> TYPE: PRT
<213> ORGANISM: Artificial Sequence
<220> FEATURE:
<223> OTHER INFORMATION: Cassette

<400> SEQUENCE: 2

Asp Ala Asp Pro Thr
1               5

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
gtttgcactg gtgatgcctg cggtggtacc                               30

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
```
caggcatcac cagtgcaaac agatagaccg                                30

<210> SEQ ID NO 5
<211> LENGTH: 28
<212> TYPE: DNA
<213> ORGANISM: Artificial Sequence
<220> FEATURE:
<223> OTHER INFORMATION: Primer

<400> SEQUENCE: 5
ctacggcccc ggcaagaccg ttgacacc                                  28

<210> SEQ ID NO 6
<211> LENGTH: 29
<212> TYPE: DNA
<213> ORGANISM: Artificial Sequence
<220> FEATURE:
<223> OTHER INFORMATION: Primer

<400> SEQUENCE: 6
gtcttgccgg ggccgtagaa gtcagtgac                                 29

<210> SEQ ID NO 7
<211> LENGTH: 28
<212> TYPE: DNA
<213> ORGANISM: Artificial Sequence
<220> FEATURE:
<223> OTHER INFORMATION: Primer

<400> SEQUENCE: 7
gtacctgccc taccacttct ggggaccc                                  28

<210> SEQ ID NO 8
<211> LENGTH: 28
<212> TYPE: DNA
<213> ORGANISM: Artificial Sequence
<220> FEATURE:
<223> OTHER INFORMATION: Primer

<400> SEQUENCE: 8
gaagtggtag ggcaggtacc acgacgag                                  28

<210> SEQ ID NO 9
<211> LENGTH: 40
<212> TYPE: DNA
<213> ORGANISM: Artificial Sequence
<220> FEATURE:
<223> OTHER INFORMATION: Primer

<400> SEQUENCE: 9
gacgcggatc ctaccacccc cggtgccgct cgtggtacct                     40

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10
tgtagggtag gtgctgtcga gccag                                     25

<210> SEQ ID NO 11
<211> LENGTH: 4
<212> TYPE: PRT
<213> ORGANISM: Artificial Sequence

```
<220> FEATURE:
<223> OTHER INFORMATION: Fragment

<400> SEQUENCE: 11

Asn Ala Thr Gly
1

<210> SEQ ID NO 12
<211> LENGTH: 5
<212> TYPE: PRT
<213> ORGANISM: Artificial Sequence
<220> FEATURE:
<223> OTHER INFORMATION: fragment

<400> SEQUENCE: 12

Asp Ala Asp Pro Thr
1               5

<210> SEQ ID NO 13
<211> LENGTH: 43
<212> TYPE: DNA
<213> ORGANISM: artificial
<220> FEATURE:
<223> OTHER INFORMATION: Primer

<400> SEQUENCE: 13
caagaatgca ccgctcctgg tagctgcacc acaaactccg gtg                           43

<210> SEQ ID NO 14
<211> LENGTH: 24
<212> TYPE: DNA
<213> ORGANISM: Artificial
<220> FEATURE:
<223> OTHER INFORMATION: Primer

<400> SEQUENCE: 14
ccagctcaga gagggatggg tttc                                                24

<210> SEQ ID NO 15
<211> LENGTH: 27
<212> TYPE: DNA
<213> ORGANISM: Artificial
<220> FEATURE:
<223> OTHER INFORMATION: Primer

<400> SEQUENCE: 15
caaaacggtg ccattacgtt agatgcc                                             27

<210> SEQ ID NO 16
<211> LENGTH: 24
<212> TYPE: DNA
<213> ORGANISM: artificial
<220> FEATURE:
<223> OTHER INFORMATION: Primer

<400> SEQUENCE: 16
gtggtgcagc taccaggagc ggtg                                                24

<210> SEQ ID NO 17
<211> LENGTH: 13
<212> TYPE: PRT
<213> ORGANISM: artificial
<220> FEATURE:
<223> OTHER INFORMATION: fragment

<400> SEQUENCE: 17
```

```
Ser Thr Cys Lys Ser Gly Gly Ser Cys Thr Thr Asn Ser
1               5                   10
```

<210> SEQ ID NO 18
<211> LENGTH: 13
<212> TYPE: PRT
<213> ORGANISM: artificial
<220> FEATURE:
<223> OTHER INFORMATION: fragment

<400> SEQUENCE: 18

```
Gln Glu Cys Thr Ala Pro Gly Ser Cys Thr Thr Gln Asn
1               5                   10
```

CELLOBIOHYDROLASE HAVING IMPROVED THERMAL STABILITY

SEQUENCE LISTING SUBMISSION VIA EFS WEB

A computer readable text file, entitled "020463-5010_SequenceListing.txt," created on or about Nov. 23, 2016 with a file size of about 8 KB contains the sequence listing for this application and is hereby incorporated by reference in its entirety.

TECHNICAL FIELD

The present invention relates to cellobiohydrolase with improved thermal stability and to technology applying it.

BACKGROUND ART

Although various techniques for saccharifying cellulose are available, the enzymatic saccharification technique, which requires less energy but produces a high yield of sugar, has been in the mainstream of development. Cellulase, which is a cellulose-degrading enzyme, is broadly divided into cellobiohydrolases, which act on the crystalline regions of cellulose (and may be referred to as "CBH" in this specification), and endoglucanases, which act inside the cellulose molecular chain to reduce the molecular weight. β-glucosidase acts on a hydrosoluble oligosaccharide or cellobiose to catalyze the hydrolysis of their β-glycosidic bonds. Of these, cellobiohydrolases are most important for efficient saccharification and are being used in great amounts because cellobiohydrolases act on the crystalline regions of cellulose to hydrolyze the cellulose from its end. CBH is divided into two types, CBHI and CBHII, based on the difference in action mechanism. CBHI, an enzyme classified into GH7, cleaves a cellulose chain from its reducing end into cellobiose units. CBHI has a tunnel structure with four long loops that cover the active site and substrate-binding site. A cellulose chain can pass through the tunnel and is cleaved from its end into cellobiose units. CBHII is an enzyme classified into GH6, and cleaves a cellulose chain from its non-reducing end into cellobiose units. CBHII has two loops covering the active site, and the catalytic site forms a tunnel structure because of the loops.

Saccharification of biomass using the group of enzymes needs to be more efficient. In particular, improving the thermal stability (heat resistance) of the enzymes will enable contamination prevention, increased reaction efficiency, and more efficient saccharification through recycling of the enzymes.

CITATION LIST

Patent Literature

Patent Literature 1: JP2001-17180A

Non-Patent Literature

Non-patent Literature 1: Inoue et al., J. Ind. Microbiol. Biotechnol. 2013 August; 40(8): 823-30.
Non-patent Literature 2: Kishishita et al., Protein Expr Purif. 2014 February; 94:40-5.
Non-patent Literature 3: Grassick et al., European Journal of Biochemistry Volume 271, Issue 22, pages 4495-4506, November 2004

SUMMARY OF INVENTION

Technical Problem

In view of the state of the art, an object of the present invention is to provide CBHI excellent in thermal stability.

Solution to Problem

The present inventors conducted extensive research to achieve the object, and found that substituting one or more specific amino acid residues in the amino acid sequence of CBHI originated from *Talaromyces cellulolyticus* can markedly improve its thermal stability while maintaining the enzyme activity. The inventors conducted further research on the basis of the findings and completed the present invention. The following describes typical embodiments of the present invention.

Item 1. A polypeptide comprising the following mutation (A) and/or (B) in the amino acid sequence set forth in SEQ ID NO: 1, an amino acid sequence having at least 85% identity with the amino acid sequence set forth in SEQ ID NO: 1, or the amino acid sequence set forth in SEQ ID NO: 1 having substitution, insertion, addition, and/or deletion of one or several amino acid residues, (A): at least one amino acid residue substitution selected from the group consisting of S42Q, T43E, K45T, S46A, G47P, N53Q, S54N, T262G, S298P, A426P, and V451F, and (B): substitution of an amino acid region from position 413 to position 416 in the amino acid sequence set forth in SEQ ID NO: 1 with an amino acid sequence set forth in SEQ ID NO: 2, the polypeptide having cellobiohydrolase activity and improved thermal stability.

Item 2. A polynucleotide encoding the polypeptide according to Item 1.

Item 3. An expression vector incorporating the polynucleotide according to Item 2.

Item 4. A transformant obtained by transformation with the vector according to Item 3.

Item 5. A method for producing the polypeptide according to Item 1, the method comprising culturing the transformant according to Item 4.

Item 6. A method for producing cellobiose, the method comprising allowing the polypeptide according to Item 1 to act on a sample containing cellulose.

Advantageous Effects of Invention

A cellobiohydrolase excellent in thermal stability is obtained by following the present invention. Thus, use of the present invention can efficiently saccharify biomass.

DESCRIPTION OF EMBODIMENTS

Figure 1:
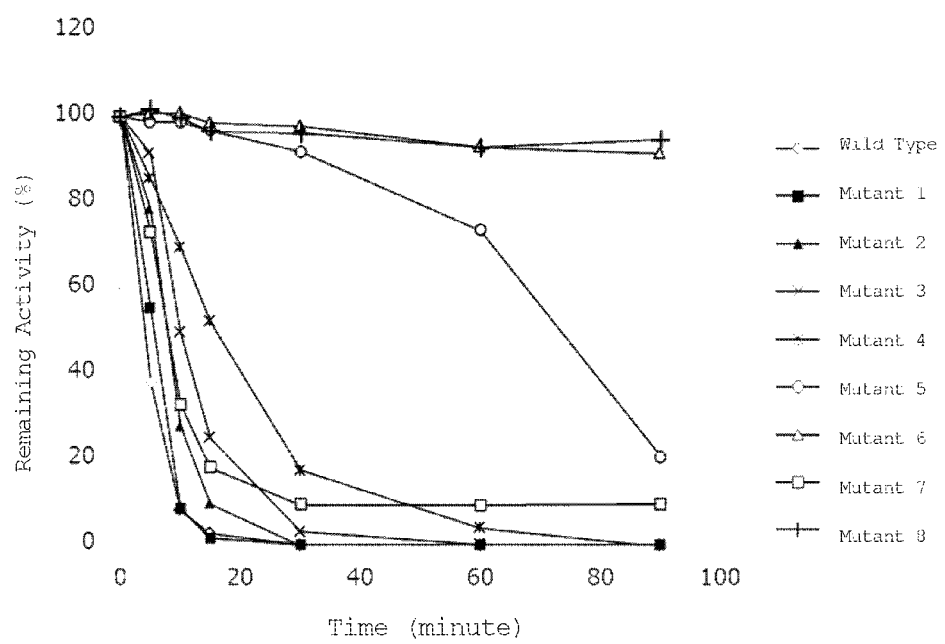
FIG. 1 shows the measurement results of the remaining activity of CBHI after heat treatment.

The amino acid sequence set forth in SEQ ID NO: 1 is an amino acid sequence constituting the wild-type CBHI originated from *Talaromyces cellulolyticus*, which is a filamentous fungus. The sequence is known.

CBHI with improved thermal stability is preferably a polypeptide comprising an amino acid sequence having specific amino acid residue substitution, described later, in the amino acid sequence set forth in SEQ ID NO: 1, an amino acid sequence having at least 85% identity with the amino acid sequence set forth in SEQ ID NO: 1, or the amino acid sequence set forth in SEQ ID NO: 1 having substitution, insertion, addition, and/or deletion of one or several amino acid residues. In this specification, an "amino acid sequence having at least 85% identity with the amino acid sequence set forth in SEQ ID NO: 1" and the "amino acid sequence set forth in SEQ ID NO: 1 having substitution, insertion, addition, and/or deletion of one or several amino acid residues" may be collectively referred to as an "amino acid sequence equivalent to SEQ ID NO: 1."

The amino acid sequence identity can be determined by using a commercially available analytical tool or an analytical tool available through telecommunication lines (Internet). For example, the amino acid sequence identity can be determined by using ClustalW Ver. 2.1 Pairwise Alignment (clustalw.ddbj.nig.ac.jp/index.php?lang=ja) with default parameters. Alternatively, the amino acid sequence identity can be determined by using the Basic Local Alignment Search Tool (BLAST) available from the National Center for Biotechnology Information (NCBI) with default parameters (default setting).

In an embodiment, the amino acid sequence having at least 85% identity with the amino acid sequence set forth in SEQ ID NO: 1 has preferably at least 90% identity with the amino acid sequence set forth in SEQ ID NO: 1, more preferably at least 95% identity with the amino acid sequence set forth in SEQ ID NO: 1, still more preferably at least 98% identity with the amino acid sequence set forth in SEQ ID NO: 1, and yet more preferably at least 99% identity with the amino acid sequence set forth in SEQ ID NO: 1.

In the "amino acid sequence set forth in SEQ ID NO: 1 having substitution, insertion, addition, and/or deletion of one or several amino acid residues" described above, the term "several" is not particularly limited, insofar as the CBHI has cellobiohydrolase activity and improved thermal stability. For example, the term "several" refers to 50, 45, 30, 25, 20, 15, 10, 5, 3, or 2. The term "several" as used here does not include the number of amino acid residues substituted to improve thermal stability, which are described later.

When one or several amino acid residues in the amino acid sequence set forth in SEQ ID NO: 1 are substituted, the type of substitution is preferably, but not particularly limited to, conservative amino acid substitution from the standpoint that the higher-order structure, phenotype, or properties of the polypeptide are not adversely affected in a significant manner. The term "conservative amino acid substitution" refers to substitution of an amino acid residue with another amino acid residue having a side chain of similar nature. According to their side chains, amino acid residues can be classified into basic side chains (e.g., lysine, arginine, and histidine), acidic side chains (e.g., aspartic acid, and glutamic acid), uncharged polar side chains (e.g., glycine, asparagine, glutamine, serine, threonine, tyrosine, and cysteine), nonpolar side chains (e.g., alanine, valine, leucine, isoleucine, proline, phenylalanine, methionine, and tryptophan), β-branched side chains (e.g., threonine, valine, and isoleucine), and aromatic side chains (e.g., tyrosine, phenylalanine, tryptophan, and histidine). Thus, substitution of an amino acid residue is preferably made such that an original amino acid residue is substituted with another amino acid residue belonging to the same category as that of the original amino acid residue of the original amino acid sequence. This "substitution" differs from the substitution made to improve thermal stability, which is described later.

Mutations such as substitution, deletion, insertion and/or addition, or the like of one or several amino acid residues are made preferably in the regions that are not significantly essential for the higher-order structure of the polypeptide, or in the regions that are not directly associated with its catalytic activity (e.g., regions other than the active center). Examples of such regions include regions exposed on the surface of protein.

It is known in the art how to make a mutation such as substitution, deletion, insertion, or addition of one or several amino acid residues in a specific amino acid sequence, and any technique can be used. Such a mutation can be made by using, for example, the restriction enzyme treatment, the treatment using an exonuclease, DNA ligase, etc., site-directed mutagenesis, or random mutagenesis.

The substitution made to improve thermal stability of CBHI (the specific substitution mentioned above) refers to (A) at least one amino acid residue substitution selected from the group consisting of S42Q, T43E, K45T, S46A, G47P, N53Q, S54N, T262G, S298P, A426P, and V451F, and/or (B) substitution of an amino acid region from position 413 to position 416 in the amino acid sequence set forth in SEQ ID NO: 1 with an amino acid sequence set forth in SEQ ID NO: 2. Regarding the codes that represent each type of substitution (A), the number indicates the position of an amino acid residue in the amino acid sequence of SEQ ID NO: 1. The letter before the number indicates the type of the amino acid residue originally present at the position. The letter after the number indicates the type of the amino acid residue that substitutes the original amino acid residue. For example, "S42Q" means that serine (S) at position 42 in the amino acid sequence of SEQ ID NO: 1 is substituted with glutamine (Q). The other codes representing substitution are interpreted in the same manner.

In substitution (B), the amino acid sequence from position 413 to position 416 in the amino acid sequence set forth in SEQ ID NO: 1 is NATG (SEQ ID NO: 11). The amino acid sequence set forth in SEQ ID NO: 2 that substitutes this region is DADPT.

In the specific amino acid residue substitution (A) and (B), only one type of substitution may be present in the amino acid sequence of SEQ ID NO: 1 or an amino acid sequence equivalent to SEQ ID NO: 1. A combination of two or more types of substitution may be present in the amino acid sequence of SEQ ID NO: 1 or an amino acid sequence equivalent to SEQ ID NO: 1. When a combination of two or more types of amino acid residue substitution is added to the amino acid sequence of SEQ ID NO: 1 or an amino acid sequence equivalent to SEQ ID NO: 1, the combination can be any combination. The number of amino acid substitution types to be combined can also be any number. For example, the number is 2 types or more, 3 types or more, 4 types or more, 5 types or more, 6 types or more, 7 types or more, 8 types or more, 9 types or more, 10 types or more, 11 types or more, or all 12 types.

In an embodiment, a preferable combination of amino acid substitution is composed of S42Q, T43E, K45T, S46A, G47P, N53Q, and S54N. In an embodiment, a preferable combination of amino acid substitution is composed of T262G, S298P, and A426P. In an embodiment, a preferable combination of amino acid substitution is composed of T262G, S298P, A426P, N413D, T415D, and G416P.

Incorporating the specific amino acid substitution described above into the amino acid sequence set forth in SEQ ID NO: 1 or an amino acid sequence equivalent to SEQ ID NO: 1 enables the polypeptide to exhibit improved thermal stability. Improved thermal stability means that such a CBHI has a higher thermal stability than the wild-type CBHI having the amino acid sequence set forth in SEQ ID NO: 1 (i.e., at the same temperature, such a CBHI is more unlikely to be inactivated than the wild-type CBHI).

The thermal stability can be measured by any technique. For example, the thermal stability can be determined by measuring the temperature at which the steric structure of the protein changes using the protein thermal shift assay (Kishishita et al., Protein Expr Purif. 2014 February; 94:40-5.) used in the Examples described later. In the use of this measurement technique, since the denaturation temperature of the wild-type CBHI is 63° C., CBHI with improved thermal stability preferably has a denaturation temperature of more than 63° C. Such a denaturation temperature is, for example, 64° C. or more, 65° C. or more, 66° C. or more, 67° C. or more, 68° C. or more, 69° C. or more, 70° C. or more, 71° C. or more, 72° C. or more, 73° C. or more, 74° C. or more, and 75° C. or more.

The thermal stability can also be evaluated by maintaining CBHI at a predetermined temperature for a predetermined time period (heat treatment) and measuring the enzyme activity before and after the treatment to determine the thermal stability on the basis of the remaining activity after heat treatment. When the remaining activity is higher than the remaining activity of the wild-type CBHI, the thermal stability is determined to be improved. For example, as described in the Examples below, when CBHI is maintained at 65° C. for 5 minutes, the remaining activity of CBHI is preferably 50% or more, more preferably 55' or more, still more preferably 60% or more, and yet more preferably 70% or more.

As used here, "activity" and "enzyme activity" refer to cellobiohydrolase activity unless otherwise indicated. Methods for measuring the cellobiohydrolase activity are known, and any method can be selected for measurement. Examples include a method comprising measuring free PNP using, as a substrate, a synthetic substrate PNP-Lac used in the Examples described later.

The polypeptide of CBHI with improved thermal stability can be produced in accordance with a genetic engineering procedure, using the polynucleotide that encodes the polypeptide. The polypeptide can also be produced on the basis of the information of the amino acid sequence set forth in SEQ ID NO: 1, using an ordinary protein chemical synthesis method (e.g., liquid-phase method and solid-phase method).

The polynucleotide encoding the polypeptide of CBHI with improved thermal stability can be easily obtained by designing a polynucleotide on the basis of the base sequence encoding the amino acid sequence set forth in SEQ ID NO: 1, taking into consideration the types and positions of introduced substitution and other mutations, and creating the polynucleotide using a chemical DNA synthesis method (e.g., phosphoramidite method) or a genetic engineering procedure. The polynucleotide is preferably present in an isolated state. The base sequence encoding the amino acid sequence set forth in SEQ ID NO: 1 is known.

The polypeptide can be produced by inserting the polynucleotide in an expressible state into a vector, introducing the vector into a host suitable for the type of the vector, and allowing the polynucleotide to express the polypeptide.

The type of the vector is suitably selected according to the type of the host cell. Examples of vectors include plasmid vectors, cosmid vectors, phage vectors, and virus vectors (e.g., adenoviral vectors, retroviral vectors, and herpes viral vectors).

The host cell for use in introduction of the expression vector is not particularly limited as long as the polypeptide can be produced, and either prokaryotic cells or eukaryotic cells can be used. Specific examples of host cells include prokaryotic cells including bacteria of genus *Escherichia coli* such as *Escherichia coli* (e.g., HB101, MC1061, JM109, CJ236, and MV1184), coryneform bacteria such as *Corynebacterium glutamicum*, actinomycetes such as bacteria of genus *Streptomyces*, bacteria of genus *Bacillus* such as *Bacillus subtilis*, bacteria of genus *Streptococcus*, and bacteria of genus *Staphylococcus*; yeast such as genus *Saccharomyces*, genus *Pichia*, and genus *Kluyveromyces*, and fungal cells such as genus *Aspergillus*, genus *Penicillium*, genus *Trichoderma*, and genus *Acremonium*; insect cells including *Drosophila* S2, *Spodoptera* Sf9, and silkworm-culturing cells; and plant cells. It is also possible to produce the polypeptide in a medium by exploiting the protein secretory capacity of *Bacillus subtilis*, yeast, *Aspergillus oryzae*, actinomycetes, and the like.

To introduce the expression vector into a host cell, a conventional method can be used. Examples include a variety of methods such as the competent cell method, the protoplast method, the electroporation method, the microinjection method, and the liposome fusion method. Specific examples of methods for introducing the expression vector into coryneform bacteria include, but are not limited to, the protoplast method (Gene, 39, 281-286, 1985) and the electroporation method (Bio/Technology, 7, 1067-1070, 1989).

The host cell into which the expression vector has been introduced (e.g., transformant) can be used to produce the polypeptide of CBHI with improved thermal stability. The transformant can also be used to saccharify biomass containing cellulose.

The production of the polypeptide using the transformant can be performed by culturing the transformant and collecting the polypeptide from the cultured product. The culture can be performed using a passage culture or batch culture with a medium suitable for the host cell. The culture can be performed until a sufficient amount of the polypeptide is produced, with monitoring of the activity of the polypeptide produced inside and outside of the transformant as a guide.

The culture medium may be suitably selected from conventionally used media according to the host cell. The culture can be performed under conditions suitable for growth of the host cell. Examples of media used for culturing *Escherichia coli* include nutrient media such as LB medium, and minimal media to which a carbon source, a nitrogen source, a vitamin source, and the like are added, such as M9 medium.

The culture conditions can also be suitably determined according to the type of the host cell. The culture is typically performed at 16 to 42° C., preferably 25 to 37° C., for 5 to 168 hours, preferably for 8 to 72 hours. Depending on the host, either shaking culture or static culture can be used. Agitation may optionally be applied, and ventilation may optionally be provided. When an induction promoter is used, a promoter-inducing agent may be added to the medium to perform a culture.

Purification or isolation of the polypeptide from the cultured product can be performed by suitably combining known techniques. Examples of techniques for use include ammonium sulfate precipitation, solvent precipitation (e.g., ethanol), dialysis, ultrafiltration, acid extraction, and a variety of chromatographic approaches (e.g., gel filtration chromatography, anion- or cation-exchange chromatography, phosphocellulose chromatography, hydrophobic interaction chromatography, affinity chromatography, hydroxyapatite chromatography, lectin chromatography, and high-performance liquid chromatography). Examples of carriers used in affinity chromatography include carriers to which an antibody against the polypeptide is bound and carriers to which a substance with affinity for a tag is bound when the tag is added to the polypeptide.

When the polypeptide is accumulated inside the host cells, the transformed cells are disrupted, and the polypeptide is purified or isolated from the centrifuged supernatant of the disrupted product by the techniques described above. For example, after completion of culture, the cells collected by centrifugation are suspended in a buffer for cell disruption (20 to 100 mM Tris-HCl (pH of 8.0), 5 mM EDTA) and disrupted by ultrasonication. The disruption-treated fluid is centrifuged at 10000 to 15000 rpm for 10 to 15 minutes to thereby obtain a supernatant. The precipitate obtained after centrifugation can optionally be solubilized with guanidinium chloride, urea, or the like, and then further purified.

Contacting the polypeptide with a sample containing cellulose (e.g., a cellulose-based biomass resource) decomposes the biomass resource to produce molasses. When the polypeptide is used to saccharify a biomass resource, other enzymes, such as other cellulases, may be used in combination with the polypeptide to produce molasses more efficiently.

The type of cellulose-based biomass is not particularly limited, as long as the biomass can be decomposed by CBHI. Examples of cellulose-based biomass include bagasse, wood, bran, wheat straw, rice straw, chaff, soybean meal, soy pulp, coffee grounds, and rice bran.

When contacting the polypeptide with cellulose in an aqueous solution, it is preferable to set the pH and temperature of the reaction solution within the range where CBHI is not inactivated. Because the thermal stability is improved, it is preferable to perform reaction at an optimum temperature or around the optimum temperature from the standpoint of efficient sample decomposition and molasses production. For example, the temperature can be set to 5 to 90° C., preferably 15 to 80° C., more preferably 30 to 75° C., and more preferably 50 to 70° C. or 50 to 65° C. In an embodiment, the temperature can be set to 63° C. or more, 64° C. or more, 65° C. or more, or 66° C. or more. The reaction can be performed at a pH of 4 to 9. There is no particular limitation to the amount of the polypeptide to be added, and the amount can be within the range of, for example, 0.1 to 0.5% (w/w).

EXAMPLES

The following Examples describe the present invention in more detail. However, the present invention is not limited to the Examples.

The steric structure of the active domain of *Talaromyces cellulolyticus*-originated CBHI was predicted using structural coordinate data of the active domain of *Talaromyces cellulolyticus*-originated CBHI, and model building was performed. Subsequently, the active domain structure of *Talaromyces cellulolyticus*-originated CBHI was compared with the active domain structure of *Talaromyces emersonii*-originated CBHI to search for the site thought to affect the stability of *Talaromyces cellulolyticus*-originated CBHI. Using the obtained comparison information on the structure and protein stabilizing principle (e.g., hydrophobic interaction, enhancement of hydrogen bond, and stabilization of peptide loop structure using proline), amino acid residue substitution was performed on *Talaromyces cellulolyticus*-originated CBHI in a protein engineering manner. Specifically, the mutations described later were introduced.

The gene (polynucleotide) encoding *Talaromyces cellulolyticus*-originated CBHI was cloned, and fused downstream of the *Talaromyces cellulolyticus*-originated starch-inducible glucoamylase promoter and the signal sequence of the CBHI to construct an expression plasmid vector (Inoue et al., J. Ind. Microbiol. Biotechnol., 2013, 40: 823-830). *Escherichia coli* (DH5α) was then transformed using this expression vector. The obtained plasmid was purified, and mutation was introduced into the gene by the QuikChange method using this plasmid as a template. The primer sets shown in Table 1 below were used singly or in combination to introduce mutation, thereby preparing the following mutants of the amino acid sequence set forth in SEQ ID NO: 1: mutant 1 in which threonine at position 262 is substituted with glycine; mutant 2 in which serine at position 298 is substituted with proline; mutant 3 in which alanine at position 426 is substituted with proline; mutant 4 in which asparagine at position 413 is substituted with aspartic acid, threonine at position 415 is substituted with aspartic acid, and glycine at position 416 is substituted with proline; mutant 5 in which the mutations of mutants 1 to 3 are present in combination; mutant 6 in which the mutations of mutants 1 to 4 are present in combination; mutant 7 in which serine at position 42 is substituted with glutamine, threonine at position 43 is substituted with glutamic acid, lysine at position 45 is substituted with threonine, serine at position 46 is substituted with alanine, glycine at position 47 is substituted with proline, asparagine at position 53 is substituted with glutamine, and serine at position 54 is substituted with asparagine; and mutant 8 in which mutations of mutants 1 to 4 and mutant 7 are present in combination.

TABLE 1

| Set No. | F/R | Sequence | Mutation |
|---|---|---|---|
| M1 | F | GTTTGCACTGGTGAT GCCTGCGGTGGTACC (SEQ ID NO. 3) | T262G |
| | R | CAGGCATCACCAGTG CAAACAGATAGACCG (SEQ ID NO. 4) | |
| M2 | F | CTACGGCCCCGGCAA GACCGTTGACACC (SEQ ID NO. 5) | S298P |
| | R | GTCTTGCCGGGGCCG TAGAAGTCAGTGAC (SEQ ID NO. 6) | |
| M3 | F | GTACCTGCCCTACCA CTTCTGGGGACCC (SEQ ID NO. 7) | A426P |
| | R | GAAGTGGTAGGGCAG GTACCACGACGAG (SEQ ID NO. 8) | |
| M4 | F | GACGCGGATCCTACC ACCCCCGGTGCCGCT CGTGGTACCT (SEQ ID NO. 9) | NATG (413-416) (SEQ ID NO. 11) → DADPT (413-417) (SEQ ID NO. 12) |
| | R | TGTAGGGTAGGTGCT GTCGAGCCAG (SEQ ID NO. 10) | |
| M5 | F1 | CAAGAATGCACCGCT CCTGGTAGCTGCACC ACAAACTCCGGTG (SEQ ID NO. 13) | STCKSGGSCTTNS (42-54) (SEQ ID NO. 17) → QECTAPGSCTTQN |

TABLE 1-continued

| Set No. | F/R | Sequence | Mutation |
|---------|-----|----------|----------|
|  | R1 | CCAGCTCAGAGAGGG ATGGGTTTC (SEQ ID NO. 14) | (SEQ ID NO. 18) |
|  | F2 | CAAAACGGTGCCATT ACGTTAGATGCC (SEQ ID NO. 15) |  |
|  | R2 | TGTGGTGCAGCTACC AGGAGCGGTG (SEQ ID NO. 16) |  |

To prepare mutant 7, the following primer sets were used: a primer set (F1 and F2) for the substitution of the amino acid residues at positions 42 to 47 and a primer set (F2 and F2) for the substitution of the amino acid residues at positions 53 and 54.

The sequence of the mutation-introduced genes was confirmed with sequencing, and *Talaromyces cellulolyticus* was transformed with the gene-incorporated plasmids. The transformants were cultured in a starch medium to allow them to secrete mutant CBHI to the outside of the fungus. The culture solutions were collected, and ammonium sulfate was added to achieve 60% saturation. The precipitates were collected with a centrifugal separator, and dissolved in a 20 mM MES buffer (pH of 6.5), followed by desalting using a desalting column (HiPrep desalting 26/10) equilibrated with the same buffer. The desalted samples were applied to an ion-exchange column (Resource Q) equilibrated with a 20 mM MES buffer (pH of 6.5), and eluted with a 20 mM MES buffer (pH of 6.5) containing 1M sodium chloride. Ammonium sulfate was added to the eluate fractions exhibiting CBH1 activity so that the concentration became 1.2 M, and the result was applied to a hydrophobic column (Resource Iso) equilibrated with a 20 mM sodium acetate buffer (pH of 5.5) containing 1.2 M ammonium sulfate, followed by elution with a 20 mM sodium acetate buffer (pH of 5.5) to concentrate the factions exhibiting the activity. After the fractions gave a single band on SDS-PAGE, the purification was completed. The thus-purified enzymes were measured for their heat resistance and activity.

The enzyme activity was determined by measuring free PNP using a synthetic substrate PNP-Lac. The heat resistance was evaluated by measuring the denaturation temperature (Tm) at which the steric structure of the enzyme proteins change using a protein thermal shift assay (TSA) prescribed in Kishishita et al., (Protein Expr Purif. 2014 February; 94:40-5.). TSA was performed using solutions of CBHI mutated enzymes in a 20 mM sodium acetate buffer (pH of 5.0). Table 2 shows the measurement results.

TABLE 2

| Name | Type of Mutation | Mutation | Relative Activity (%) | Tm (° C.) |
|------|------------------|----------|----------------------|-----------|
| Wild Type | — | None | 100 | 65.50 |
| Mutant 1 | M1 | T262G | 94 | 66.00 |
| Mutant 2 | M2 | S298P | 88 | 68.00 |
| Mutant 3 | M3 | A426P | 87 | 67.00 |
| Mutant 4 | M4 | TNATGT (412-417)→ TDADPTT (412-418) | 98 | 68.50 |
| Mutant 5 | M1-M2-M3 | T262G, S298P, A426P | 96 | 70.67 |
| Mutant 6 | M1-M2-M3-M4 | T262G, S298P, A426P, NATG (413-416)→ DADPT (413-417) | 95 | 72.50 |
| Mutant 7 | M5 | STCKSGGSCTTNS (42-54)→ QECTAPGSCTTQN (42-54) | 93 | 65.50 |
| Mutant 8 | M1-M2-M3-M4-M5 | T262G, S298P, A426P, NATG (413-416)→ DADPT (413-417), STCKSGGSCTTNS (42-54)→ QECTAPGSCTTQN (42-54) | 95 | 72.50 |
| Trichoderma-originated CBHI | | None | — | 60.5 |

As shown in Table 2, mutants 1 to 8 all exhibited improved heat resistance (thermal stability) compared with a wild-type enzyme. In particular, mutants 4 to 6 and 8, which incorporated multiple mutations, exhibited significant improvement in thermal stability. Although mutants 1 to 8 had a slightly lower enzyme activity than the wild-type enzyme, the difference is negligible given the improved thermal stability.

Subsequently, a 20 mM sodium acetate buffer (pH of 5.0) containing any of the wild-type CBHI and mutants 1 to 8 at a concentration of 0.02 to 0.05 mg/ml was prepared. This enzyme solution was maintained at a temperature of 65° C., and a portion of the solution was taken out at a time point of 1 minute after, 5 minutes after, 10 minutes after, 15 minutes after, 30 minutes after, 60 minutes after, and 90 minutes after to measure the remaining activity at 45° C. The measurement was performed in the same manner as above using 1 mM of PNP-Lactose as a substrate. The remaining activity was calculated based on the activity at the starting point of the treatment at 65° C. (i.e., 0 minutes) taken as 100%. FIG. 1 shows the results. As is clear from FIG. 1, while the remaining activity 5 minutes after heating was 40% in the wild-type enzyme, the remaining activity was 55% in mutant 1, 80% in mutant 2, 80 to 90% in mutants 3 and 4, 100% in mutants 5, 6, and 8, and 73% in mutant 7. In particular, mutants 6 and 8 did not show a decrease in activity even 60 minutes after.

Figure 2:
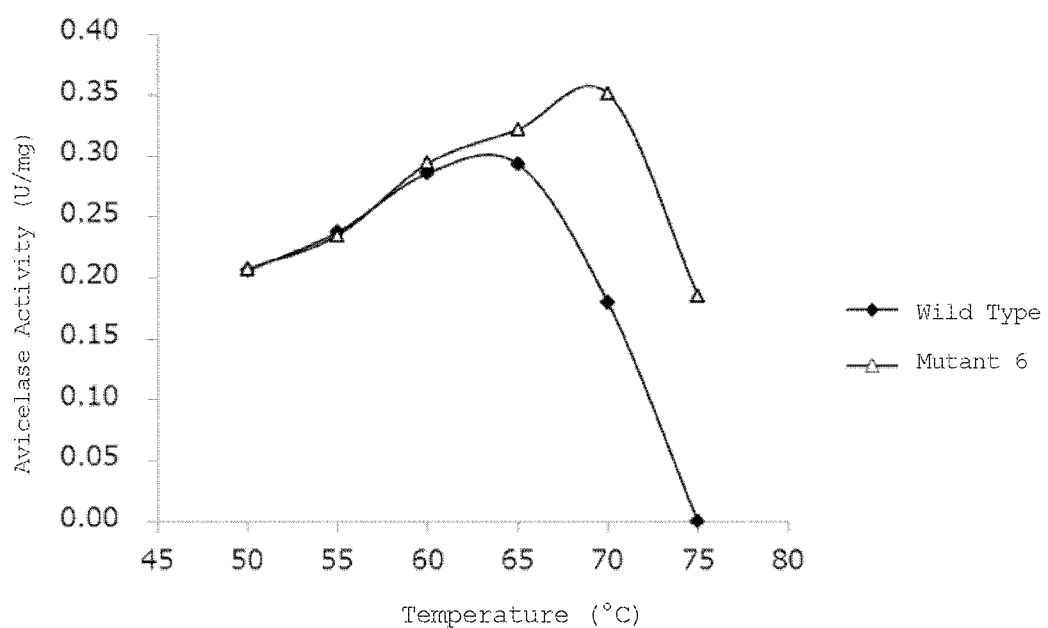
FIG. 2 shows the results of the investigation into the optimum temperature of mutant 6 and a wild-type CBHI when microcrystalline cellulose was their substrate.

In addition, the optimum temperature for mutant 6 and the wild-type CBHI was studied using microcrystalline cellulose (Avicel) (FIG. 2). Mutant 6 and the wild-type CBHI were individually subjected to reaction in a buffer (pH of 5.0) containing a microcrystalline cellulose (Avicel) substrate at 50° C. to 75° C. for 2 hours, and the liberating solubilized sugar was quantified by reducing power. As shown in FIG. 2, the results reveal that mutant 6 had a higher optimum temperature than the wild-type enzyme, even when microcrystalline cellulose was used as substrate. A similar trend is expected in other mutants.

The invention claimed is:

1. A mutant polypeptide comprising
   (i) a first mutant of SEQ ID NO: 1 having one or more mutations consisting of mutation (A) or mutation (B) or mutations (A) and (B) with reference to SEQ ID NO: 1, wherein
      the mutant (A) is at least one amino acid residue substitution selected from the group consisting of S42Q, T43E, K45T, S46A, G47P, N53Q, S54N, T262G, S298P, A426P, and V451F, and
      the mutant (B) is substitution of an amino acid region from position 413 to position 416 in the amino acid sequence set forth in SEQ ID NO: 1 with an amino acid sequence set forth in SEQ ID NO: 2;
   (ii) a second mutant amino acid sequence having at least 85% identity with the amino acid sequence of SEQ ID NO: 1, wherein the second mutant amino acid sequence has at least one amino acid residue substitution selected from the group consisting of S42Q, T43E, K45T, S46A, G47P, N53Q, S54N, T262G, S298P, and V451F with reference to SEQ ID NO: 1; or
   (iii) a third mutant amino acid sequence having at least 85% identity with the amino acid sequence of SEQ ID NO: 1, wherein the third mutant amino acid sequence has SEQ ID NO: 2 as substitution in an amino acid region corresponding to position 413 to position 416 of SEQ ID NO: 1.

2. A polynucleotide encoding the mutant polypeptide according to claim 1.

3. An expression vector incorporating the mutant polynucleotide according to claim 2.

4. An isolated host cell transformed with the expression vector according to claim 3.

5. A method for producing the mutant polypeptide according to claim 1, the method comprising culturing an isolated host cell transformed with the expression vector incorporating the polynucleotide encoding the polypeptide.

6. A method for producing cellobiose, the method comprising allowing the mutant polypeptide according to claim 1 to act on a sample containing cellulose.

7. The mutant polypeptide according to claim 1, wherein the mutant polypeptide comprises (i) the first mutant of SEQ ID NO: 1, and the only mutation in the first mutant is the mutation (A).

8. The mutant polypeptide according to claim 1, wherein the mutant polypeptide comprises (i) the first mutant of SEQ ID NO: 1, and the only mutation in the first mutant is the mutation (B).

9. The mutant polypeptide according to claim 1, wherein the mutant polypeptide comprises (i) the first mutant of SEQ ID NO: 1, and the only mutations in the first mutant are T262G, S298P, A426P, and the mutation (B).

10. The mutant polypeptide according to claim 1, wherein the mutant polypeptide comprises (ii) the second mutant amino acid sequence, wherein the second amino acid sequence comprises at least one amino acid residue substitution selected from the group consisting of S42Q and T43E.

11. The mutant polypeptide according to claim 1, wherein the mutant polypeptide comprises (ii) the second mutant amino acid sequence, wherein the second amino acid sequence comprises at least one amino acid residue substitution selected from the group consisting of K45T and S46A.

12. The mutant polypeptide according to claim 1, wherein the mutant polypeptide comprises (ii) the second mutant amino acid sequence, wherein the second amino acid sequence comprises at least one amino acid residue substitution selected from the group consisting of G47P and N53Q.

13. The mutant polypeptide according to claim 1, wherein the mutant polypeptide comprises (ii) the second mutant amino acid sequence, wherein the second amino acid sequence comprises at least one amino acid residue substitution selected from the group consisting of S54N and T262G.

14. The mutant polypeptide according to claim 1, wherein the mutant polypeptide comprises (ii) the second mutant amino acid sequence, wherein the second amino acid sequence comprises at least one amino acid residue substitution selected from the group consisting of S298P, and V451F.

15. The mutant polypeptide according to claim 1, wherein the mutant polypeptide comprises (ii) the second mutant amino acid sequence, wherein
   the second mutant amino acid sequence has at least 95% identity with the amino acid sequence of SEQ ID NO: 1, and the second mutant amino acid sequence comprises at least one amino acid residue substitution selected from the group consisting of S42Q, T43E, K45T, S46A, and G47P.

16. The mutant polypeptide according to claim 1, wherein the mutant polypeptide comprises (ii) the second mutant amino acid sequence, wherein
   the second mutant amino acid sequence has at least 95% identity with the amino acid sequence of SEQ ID NO: 1, and the second mutant amino acid sequence comprises at least one amino acid residue substitution selected from the group consisting of N53Q, S54N, T262G, S298P, and V451F.

17. The mutant polypeptide according to claim 1, wherein the mutant polypeptide comprises (ii) the second mutant amino acid sequence, wherein the second mutant amino acid sequence has at least 99% identity with the amino acid sequence of SEQ ID NO: 1, and the second mutant amino acid sequence comprises at least one amino acid residue substitution selected from the group consisting of S42Q, T43E, K45T, S46A, G47P, N53Q, S54N, T262G, S298P, and V451F.

18. The mutant polypeptide according to claim 1, wherein the mutant polypeptide comprises (iii) the third mutant amino acid sequence.

19. The mutant polypeptide according to claim 1, wherein the mutant polypeptide comprises (iii) the third mutant amino acid sequence, wherein the third mutant amino acid sequence has at least 95% identity with the amino acid sequence of SEQ ID NO: 1, and the third mutant amino acid sequence has SEQ ID NO: 2 as substitution in an amino acid region corresponding to position 413 to position 416 of SEQ ID NO: 1.

20. The mutant polypeptide according to claim 1, wherein the mutant polypeptide comprises (iii) the third mutant amino acid sequence, wherein the third mutant amino acid sequence has at least 99% identity with the amino acid sequence of SEQ ID NO: 1, and the third amino acid sequence has SEQ ID NO: 2 as substitution in an amino acid region corresponding to position 413 to position 416 of SEQ ID NO: 1.

* * * * *